United States Patent
Rausch et al.

(10) Patent No.: US 7,781,624 B2
(45) Date of Patent: Aug. 24, 2010

(54) PROCESS FOR THE PREPARATION OF NITROBENZENE BY ADIABATIC NITRATION

(75) Inventors: Andreas Rausch, Neuss (DE); Thomas Knauf, Dormagen (DE); Jeffrey Bolton, Moundsville, WV (US); Alexandre Racoes, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/315,907

(22) Filed: Dec. 8, 2008

(65) Prior Publication Data

US 2009/0187051 A1 Jul. 23, 2009

(30) Foreign Application Priority Data

Dec. 11, 2007 (DE) .................. 10 2007 059 513

(51) Int. Cl.
*C07C 205/00* (2006.01)
(52) U.S. Cl. ................................................. 568/927
(58) Field of Classification Search .................. 568/927
See application file for complete search history.

(56) References Cited

U.S. PATENT DOCUMENTS

| 2,256,999 | A | | 9/1941 | Castner |
| 4,091,042 | A | | 5/1978 | Alexanderson et al. |
| 4,772,757 | A | | 9/1988 | Lailach et al. |
| 4,973,770 | A | * | 11/1990 | Evans ...................... 568/929 |
| 4,994,242 | A | | 2/1991 | Rae et al. |
| 5,313,009 | A | | 5/1994 | Guenkel et al. |
| 5,763,697 | A | | 6/1998 | Hermann et al. |
| 7,326,816 | B2 | | 2/2008 | Knauf et al. |
| 2003/0055300 | A1 | | 3/2003 | Chrisochoou et al. |
| 2007/0249873 | A1 | | 10/2007 | Knauf et al. |

* cited by examiner

*Primary Examiner*—Jafar Parsa
(74) *Attorney, Agent, or Firm*—N. Denise Brown; Noland J. Cheung

(57) ABSTRACT

This invention relates to a process for the continuous preparation of nitrobenzene. This process comprises the adiabatic nitration of benzene with a mixture of sulfuric acid and nitric acid, in which the sum of the concentrations in the reaction zone of the metal ions which form sparingly soluble metal sulfates is less than 900 mg/l, based on the volume of the aqueous phase which contains sulfuric acid.

6 Claims, No Drawings

PROCESS FOR THE PREPARATION OF NITROBENZENE BY ADIABATIC NITRATION

CROSS REFERENCE TO RELATED PATENT APPLICATION

The present patent application claims the right of priority under 35 U.S.C. §119 (a)-(d) of German Patent Application No. 10 2007 059 513.3 filed on Dec. 11, 2007.

BACKGROUND OF THE INVENTION

The present invention relates to a process for the continuous preparation of nitrobenzene by adiabatic nitration of benzene with a mixture of sulfuric acid and nitric acid in a reaction zone, in which the aqueous phase containing sulfuric acid in the reaction zone has a content of metal ions which form sparingly soluble metal sulfates of less than 900 mg/l, based on the volume of the aqueous phase containing sulfuric acid.

This invention relates to a continuous process for the preparation of nitrobenzene by adiabatic nitration of benzene by a mixture of sulfuric and nitric acid (mixed acid). Such a process was initially disclosed in U.S. Pat. No. 2,256,999, and present day embodiments are described in, for example, U.S. Pat. No. 4,091,042, U.S. Pat. No. 5,313,009 and U.S. Pat. No. 5,763,697.

The adiabatic nitration processes described have as a common feature the fact that the starting substances benzene and nitric acid are reacted in a large excess of sulfuric acid, which takes up the heat of reaction liberated and the water formed during the reaction. For carrying out the reaction, nitric acid and sulfuric acid are mixed to give so-called mixed acid, and benzene is metered into this. The benzene reacts with the nitric acid to give water and substantially nitrobenzene. The temperature of the reaction mixture and the concentrations of benzene, nitric acid and sulfuric acid are chosen such that after the reaction zone, a mixture of benzene, nitrobenzene, sulfuric acid and water is obtained, and this mixture is substantially free from nitric acid. The temperatures required for this are conventionally between 70 and 145° C. To establish the mixed acid, nitric acid of a concentration of 60 to 98 wt. % and sulfuric acid of a concentration of 60 to 96 wt. % are conventionally employed. Benzene is employed at least in the stoichiometric amount, based on the amount of nitric acid, but preferably in a 2 to 10% excess, compared with the amount of benzene required stoichiometrically. These processes and these parameters are preferably likewise realized in the process according to the invention.

The reaction zone in which benzene and nitric acid are reacted can comprise an arrangement of stirred tanks, a loop reactor or a tube reactor, as good thorough mixing is necessary for the reaction. A tube reactor in which several dispersing elements are arranged in distribution over the length of the tube reactor and ensure intensive thorough mixing of benzene, nitric acid and sulfuric acid and water is therefore preferably employed. Such a reactor and the form of dispersing elements which can be employed are described, for example, in U.S. Pat. No. 4,994,242 and in U.S. Patent Application 2003/0055300 A1. These processes and these parameters are, preferably, likewise realized in the process of the present invention.

The reaction mixture which is obtained after the reaction zone and which is substantially free from nitric acid, is fed to a phase separation apparatus in which two phases are formed. The first phase being called crude nitrobenzene and substantially comprising nitrobenzene, benzene and an amount of sulfuric acid and water dissolved in the nitrobenzene. The second phase, also called waste acid, substantially comprises water, sulfuric acid and nitrobenzene dissolved in the sulfuric acid.

The phase separation apparatus has the intended task of separating the phases of the crude nitrobenzene and the waste acid completely, so that only the physically dissolvable contents of the other particular phase cannot be separated off. Because of this physically dissolvable content, the crude nitrobenzene always contains some quantity of sulfuric acid and the waste acid always contains some quantity of crude nitrobenzene. This process and these parameters are preferably likewise realized in the process according to the invention.

In the adiabatic nitration, the crude nitrobenzene separated off in the phase separation apparatus is conventionally, and preferably, also subjected to a washing and a working up by distillation. This is described, for example, in EP 181 61 17 A1.

In adiabatic nitration, the waste acid separated off in the phase separation apparatus is conventionally, and preferably, also introduced into an apparatus for flash evaporation of the water. In this apparatus, by application of a reduced pressure and utilizing the high temperature of the waste acid which has been achieved by the adiabatic procedure, water is evaporated out of the waste acid, such that a concentrated sulfuric acid is obtained, the concentration of which substantially corresponds to the concentration before the reaction zone. According to the embodiments of the adiabatic nitration of benzene disclosed in the prior art, which are also preferably utilized in the process according to the invention, the sulfuric acid obtained by flash evaporation (i.e. the circulating acid) is collected in a buffer tank and recycled completely into the reaction zone. The heat of reaction is utilized most effectively by the complete recycling of the sulfuric acid. By recycling the sulfuric acid, a sulfuric acid circulation is formed, which substantially comprises the reaction zone, phase separation apparatus, evaporator, buffer tank and connecting lines.

It is known in the art that metal ions which form sparingly soluble metal sulfates together with sulfate in the sulfuric acid may be present in the sulfuric acid. These metals include the elements Al, Ca, Cr, Mg, Mn, Fe, Co, Ni, Cu, Sr, Cd and Ba, in particular Ca or calcium and Fe or iron. If the concentration of these metal ions which form sparingly soluble metal sulfates exceeds the solubility limit, metal sulfates precipitate in the sulfuric acid and form solids which are carried along in the circulation with the sulfuric acid, until they settle and accumulate on a surface or at a narrow point.

It is likewise known in the prior art that the solubility limit of the metal ions which form sparingly soluble metal sulfates depends greatly on the temperature of the solution, that is to say on the temperature of the sulfuric acid. Thus, metal ions dissolve less in cold sulfuric acid than in hot sulfuric acid. Consequently, metal sulfates are preferably obtained as a solid in cold sulfuric acid or at points where sulfuric acid is cooled, such as, for example, in heat exchangers. This production of solids in heat exchangers is to be regarded as problematic, since it can lead to a covering of the surface of the heat exchanger and therefore to a deterioration in the heat transfer coefficient. This production of solids also limits the possible amount of material flowing through the heat exchanger due to the reduction in the free cross-section of the lines in the heat exchanger. Table 1 shows the solubility limits (in mg/l) for calcium (Ca) and iron (Fe) for some selected temperatures (source: E K.-H. Wehde: Untersuchungen zum Löslichkeitsverhalten anorganischer Sulfate und zur Wärmeübertragung bei der Aufkonzentrierung verunreinigter Schwefelsäure, Doctorate Thesis, University of Essen, 1984, p. 65 & p. 70):

TABLE 1

Solubility limits of calcium and iron ions in 70 wt. % strength sulfuric acid

| Temperature | Calcium, $Ca^{2+}$ [mg/l] | Iron, $Fe^{2+}$ [mg/l] |
| --- | --- | --- |
| 20° C. | 105 | 300 |
| 60° C. | — | 770 |
| 100° C. | 230 | 1,670 |
| 110° C. | 260 | 2,360 |

The prior art takes into account the phenomenon described above of metal sulfates precipitating out in heat exchangers by periodic flushing of all those heat exchangers which carry circulating acid. This periodic flushing removes the metal sulfates which have crystallized out of the concentrated sulfuric acid. This is described in, for example, DE 340 97 17 C2.

Furthermore, it has now been observed that the problematic deposits of metal sulfates may occur not only in heat exchangers, but also at all points where the concentration of the metal ions which form sparingly soluble metal sulfates is high enough and the temperature is low enough to result in the formation of solid, and at the same time, at points where the flow rate of the sulfuric acid or the cross-section of the lines carrying sulfuric acid is low enough to bring about an accumulation of the metal sulfates which is troublesome for the process.

Deposits of metal sulfates can therefore be observed not only in heat exchangers, but also as deposits on the bottoms of tanks, at measurement points, such as level measurements, and on dispersing elements which, as intended, have small through-openings. Examples of such dispersing elements are described, for example, in U.S. Pat. No. 4,994,242 Deposits of metal sulfates can likewise also occur within the flash evaporator, in which, as intended, the sulfuric acid is cooled while water is evaporated and the concentration of the acid is increased. Deposits of metal salts can furthermore also form in the working up section following the reaction, such as, for example, in the waste water treatment due to entrained metal sulfates. To reduce the troublesome influence of these deposits, periodic cleaning of the installation components in question is considered necessary according to the prior art cited above. This cleaning, however, is associated with down times in the production and therefore with additional costs.

SUMMARY OF THE INVENTION

It has now been found that low contents of metal ions in the sulfuric acid obtained from the nitration have a positive effect on the concentrating of the sulfuric acid. Thus, in the flash evaporation (i.e. an evaporation associated with expansion) of the waste acid containing sulfuric acid which is obtained after the aqueous phase has been separated off from the reaction mixture obtained from the nitration of benzene, higher sulfuric acid concentrations are achieved in the concentrated sulfuric acid obtained if the content of metal ions is low. This is presumably attributed to the improved evaporability of the water in the flash evaporator at low contents of metal ions in the waste acid. Thus, it has now been found that during flash evaporation under otherwise identical conditions (i.e. the same temperature of the waste acid, same sulfuric acid content of the waste acid, same pressure in the flash evaporator), a concentrated sulfuric acid having a concentration of $H_2SO_4$ which is up to 0.25% higher is obtained if a waste acid having low contents of metal ions of less than 900 mg/l is employed. This is illustrated in Example 4 and Example 5 of the present application.

The present invention therefore is directed to a process for the continuous preparation of nitrobenzene comprising adiabatically nitrating benzene with a mixture of sulfuric acid and nitric acid. In this process, the sum of the concentrations in the reaction zone of the metal ions which form sparingly soluble metal sulfates is less than 900 mg/l, based on the volume of the aqueous phase containing sulfuric acid.

It has now furthermore been found that lower metal ion concentrations also lead to a lowering of the boiling point of the sulfuric acid, which likewise results in a low energy requirement for concentration of the sulfuric acid.

An object of the present invention was to provide an inexpensive and reliable process in which the depositing of solids and the associated risk of blockage, which can lead, for example, to the failure of measurement points, is minimized, and with which at the same time the sulfuric acid obtained, which is produced from the nitration, can be concentrated again with a low consumption of energy.

It has surprisingly been found that a cleaning of heat exchangers and lines carrying sulfuric acid to remove solid metal sulfates which have precipitated out can be dispensed with or eliminated, if in the nitration of the benzene by a mixed acid containing sulfuric acid and nitric acid, the sulfuric acid obtained again by flash evaporation of water is not completely recycled into the reaction zone as circulating acid, but is partly sluiced out and replaced by fresh sulfuric acid of low metal ion content.

In this context, the sulfuric acid is sluiced out and renewed to an extent such that the concentrations of metal ions which form sparingly soluble metal sulfates in the aqueous phase containing sulfuric acid in the reaction zone remain below the concentrations of the solubility limit. In other words, the concentrations are preferably below 100 mg/l for calcium and preferably below 300 mg/l for iron. In accordance with the present invention, preferably, the sum of the concentrations of all metal ions which form sparingly soluble metal sulfates is less than 900 mg/l, based on the aqueous phase containing sulfuric acid in the reaction zone. It is more preferred that the sum of the concentrations of all metal ions which form sparingly soluble metal sulfates is less than 500 mg/l.

An aqueous phase containing sulfuric acid in the reaction zone which contains less than 900 mg/l of metal ions which form sparingly soluble metal sulfates can be achieved by several embodiments of this invention, and specifically in an installation for the preparation of nitrobenzene by adiabatic nitration of benzene.

The present invention relates to a process for the continuous preparation of nitrobenzene by adiabatic nitration of benzene with a mixture of sulfuric acid and nitric acid, characterized in that the sum of the concentrations in the reaction zone of the metal ions which form sparingly soluble metal sulfates is less than 900 mg/l, and preferably less than 500 mg/l, based on the volume of the aqueous phase containing sulfuric acid.

In this context, the metal ions which form sparingly soluble metal sulfates are preferably Al (i.e. aluminium), Ca (i.e. calcium), Cr (i.e. chromium), Mg (i.e. magnesium), Mn (i.e. manganese), Fe (i.e. iron), Co (i.e. cobalt), Ni (i.e. nickel), Cu (i.e. copper), Sr (i.e. strontium), Cd (i.e. cadmium) and Ba (i.e. barium), and particular preferably Ca (calcium) and Fe (iron). Preferably, the sum of the total contents of these metal ions (i.e. Al, Ca, Cr, Mg, Mn, Fe, Co, Ni, Cu, Sr, Cd and Ba) present in the reaction zone is less than 800 mg/l, and more preferably, is less than 450 mg/l, based on the volume of the aqueous phase containing sulfuric acid.

DETAILED DESCRIPTION OF THE INVENTION

In accordance with the present invention, the process is preferably carried out in this context as follows:

The starting substances, benzene and nitric acid, are reacted in a large excess of sulfuric acid, which takes up the heat of reaction liberated and the water formed during the reaction. For the process of carrying out the reaction, nitric acid and sulfuric acid are mixed to give so-called mixed acid, and benzene is metered into this. The benzene reacts with the nitric acid to give water and substantially nitrobenzene. The temperature of the reaction mixture and the concentrations of benzene, nitric acid and sulfuric acid are preferably chosen such that after a reaction zone, conventionally in the nitrating reactor, a mixture of benzene, nitrobenzene, sulfuric acid and water is obtained. This mixture is substantially free from nitric acid. The temperatures required for this are conventionally between 70° and 145° C. To establish the mixed acid, nitric acid having a concentration of from 60 to 98 wt. %, and sulfuric acid having a concentration of from 60 to 96 wt. % are conventionally employed. Benzene is preferably employed at least in the stoichiometric amount, based on the amount of nitric acid. It is more preferred, however, that benzene is employed in an excess of 2 to 10%, compared with the amount of benzene required stoichiometrically.

The reaction zone in which benzene and nitric acid are reacted can comprise an arrangement of stirred tanks, a loop reactor or a tube reactor. Good thorough mixing is necessary for the reaction. Therefore, a tube reactor in which several dispersing elements are arranged to distribute materials over the length of the tube reactor and ensure intensive thorough mixing of benzene, nitric acid and sulfuric acid and water is preferably employed. Such a reactor and the form of suitable dispersing elements which can be employed in accordance with the present invention are described, for example, in U.S. Pat. No. 4,994,242 and in US Published Patent Application 2003/0055300 A1, the disclosures of which are hereby incorporated by reference.

The reaction mixture which is obtained after the reaction zone, and is substantially free from nitric acid, is fed to a phase separation apparatus in which two phases are formed. The first phase being called crude nitrobenzene, and substantially comprising nitrobenzene, benzene and an amount of sulfuric acid and water dissolved in the nitrobenzene. The second phased being called waste acid, and substantially comprising water, sulfuric acid and nitrobenzene dissolved in the sulfuric acid.

The phase separation apparatus has the intended task of separating the phases of the crude nitrobenzene and the waste acid completely, so that only the physically dissolvable contents of the other particular phase cannot be separated off. Because of this physically dissolvable content, the crude nitrobenzene always contains some quantity of sulfuric acid and the waste acid always contain some quantity of crude nitrobenzene.

In accordance with the present invention, the crude nitrobenzene which is separated off in the phase separation apparatus is then preferably subjected to a washing and/or a working up by distillation. One suitable method for washing and distillation is described, for example, in EP 181 61 17 A1 which is believed to correspond to U.S. Pat. No. 7,326,816, the disclosure of which is hereby incorporated by reference.

The waste acid separated off in the phase separation apparatus is preferably introduced into an apparatus for rapid evaporation (flash evaporation) of the water. In this apparatus, by application of a reduced pressure and utilizing the high temperature of the waste acid which has been achieved by the adiabatic procedure, water is evaporated out of the waste acid, such that a concentrated sulfuric acid is obtained. In fact, the concentration of this concentrated sulfuric acid substantially corresponds to the concentration before the reaction zone. As described in the previously known embodiments of the adiabatic nitration of benzene, which may also preferably be utilized in the process according to the invention, the sulfuric acid obtained by the evaporation is collected in a buffer tank and recycled completely into the reaction zone. The recycled sulfuric acid is also called circulating acid. The heat of reaction is utilized most effectively by the complete recycling of the sulfuric acid. By recycling the sulfuric acid, a sulfuric acid circulation is formed, which substantially comprises the reaction zone, the phase separation apparatus, the evaporator, the buffer tank and the connecting lines.

It has surprisingly been found that the nitric acid which is employed for the nitration is the essential source for the introduction of metal ions into the production installations for the preparation of nitrobenzene by adiabatic nitration of benzene. The metal ions enter into the nitric acid by corrosion (e.g. Fe, Ni, Cr, Al), where the corrosion may occur in the nitric acid installation/equipment itself, or in the transporting medium (e.g. a pipeline, a ship, etc.), or are introduced by the water employed in the preparation of nitric acid (e.g. Mg, Ca, Ba). Therefore, the concentration of metal ions in the circulating acid can be limited by using a nitric acid of high quality. In order to avoid an increase in the metal ion concentration in the circulating acid, a nitric acid which contains less than 10 mg/l, more preferably less than 5 mg/l, and most preferably less than 1 mg/l of metal ions which form sparingly soluble metal sulfates is preferably employed.

In order to rule out completely an accumulation of metal ions in the circulating acid, and therefore, also in the aqueous phase containing sulfuric acid in the reaction zone, a nitric acid which is free from metal ions would have to be employed. The preparation and transportation of such a nitric acid is not practical, however, so further measures are advantageous to achieve a low metal ion concentration in the circulating acid and in the aqueous phase containing sulfuric acid in the reaction zone.

It has also been surprisingly found that the metal ion concentrations in the concentrated and recycled sulfuric acid obtained after phase separation and concentration (circulating acid) and in the aqueous phase containing sulfuric acid in the reaction zone can be regulated most effectively if the circulating acid is not recycled completely into the reaction zone, as described in the prior art, but instead, if a portion of the circulating acid is sluiced out and replaced by a sulfuric acid of comparable or higher concentration (i.e. >65 wt. % of $H_2SO_4$) with a lower metal content. For this, the circulating acid is sluiced out at any desired point of the sulfuric acid circulation, which preferably comprises at least the reaction zone, the phase separation apparatus, the evaporator, the buffer tank and the connecting lines, and fresh sulfuric acid is fed in at any other desired point of the sulfuric acid circulation, until the desired concentration of metal ions which form sparingly soluble metal sulfates has become established, and which concentration, in accordance with the present invention, is below 900 mg/l in the aqueous phase containing sulfuric acid in the reaction zone.

For the feeding in of the fresh sulfuric acid, it must be taken into account that small amounts of circulating acid are also already withdrawn from the sulfuric acid circulation in that they leave the phase separation apparatus in solution in the crude nitrobenzene. In general, the amount of sulfuric acid dissolved in the crude nitrobenzene does not exceed a value of 0.25 wt. % of the crude nitrobenzene at the temperatures of from 120° to 145° which conventionally exist in phase separation apparatuses. Moreover, all amounts of sulfuric acid discharged with the crude nitrobenzene are not present in dissolved form but are present as a separate second phase (emulsion) in the crude nitrobenzene, and are to be understood in the context of this invention as amounts of sulfuric acid which are sluiced out.

The sluicing out of circulating acid and the feeding in of fresh sulfuric acid has proved to be effective only if the fresh sulfuric acid has a concentration of $H_2SO_4$ comparable to or higher than the circulating acid, and if the fresh sulfuric acid has a significantly lower content of metal ions than the circulating acid which is being sluiced out. According to the invention, a sulfuric acid in which the concentration of $H_2SO_4$ is preferably greater than 65 wt. %, more preferably greater than 70 wt. % and most preferably greater than 95 wt. %, and which has a content of metal ions which form sparingly soluble metal sulfates of preferably 100 mg/l or less, and more preferably of less than 50 mg/l is employed as the replacement for the circulating acid which is sluiced out.

By the use of an individual measure of the three mentioned above or preferably by combination thereof, it is ensured that a content of metal ions which form sparingly soluble metal sulfates of less than 900 mg/l is present in the aqueous phase containing sulfuric acid in the reaction zone. The utilization of such an aqueous phase or sulfuric acid in a process for the preparation of nitrobenzene by adiabatic nitration provides several advantages as described below.

Due to the low concentrations of metal ions, sparingly soluble metal sulfates no longer precipitate out in the reaction zone and also in the circulation. As a result, the cleaning of heat exchangers, measurement points and buffer tanks, which is conventionally carried out with sulfuric acid having a concentration of 96 wt. %, and which is sometimes associated with dismantling of the contaminated apparatuses, and is thus, very time-consuming and cost-intensive, is dispensed with or eliminated. Accordingly, the process according to the invention increases the availability of the installation/equipment and lowers the outlay on maintenance.

By adhering to low metal ion concentrations in the aqueous phase containing sulfuric acid in the reaction zone or in the sulfuric acid led in circulation, there is no longer the danger that such large amounts of metal sulfates are obtained in the form of solids in which the solids accumulate in the reaction zone, such as, for example, in nozzles or dispersing elements which, as intended, conventionally have small through-openings, and thereby reduces the thorough mixing in the reaction zone such that the adiabatic nitration of benzene proceeds incompletely. If this occurs, the circulating acid must be renewed completely. The complete renewal of the circulating acid is associated with a considerable outlay on labor and high storage, disposal and replacement costs. This outlay is reduced considerably by the continuous sluicing out and renewal of the circulating acid in accordance with the present invention.

By adhering to low metal ion concentrations in the aqueous phase containing sulfuric acid in the reaction zone or in the sulfuric acid led in the circulation, the sulfuric acid introduced into the flash evaporator for concentration does not have an increased heat transfer coefficient or increased boiling point. Thus there is no increased demand for energy for the concentration.

By adhering to low metal ion concentrations in the aqueous phase containing sulfuric acid in the reaction zone or in the sulfuric acid led in the circulation, the crude nitrobenzene stream obtained from the phase separation apparatus also has a lower content of metal ions, since the sulfuric acid dissolved therein or present as a second phase has a lower content of metal ions. This opens up the possibility of passing this crude nitrobenzene stream through a heat exchanger with narrow through-openings, without the fear that metal sulfates may precipitate out in this heat exchanger and potentially block it. The crude nitrobenzene which leaves the phase separation apparatus and conventionally has temperatures of between 120° and 145° C., can thus be utilized to preheat the benzene or the nitric acid fed into the reaction zone by means of a heat exchanger. This measure saves cooling costs for the crude nitrobenzene and heating costs for the circulating acid.

The process according to the invention is characterized by a number of features which are not found in the prior art. Thus, in the preparation of nitrobenzene by adiabatic nitration of benzene, a higher availability of the installation/equipment, lower maintenance costs and lower operating costs are achieved if an aqueous phase containing sulfuric acid in the reaction zone having a content of metal ions which form sparingly soluble metal sulfates of less than 900 mg/l, and preferably less than 500 mg/l is used. As a result, a crude nitrobenzene is obtained of which the heat can be utilized in a heat exchanger in order to preheat the streams of the starting substances benzene and/or nitric acid without the fear that metal sulfates precipitate out in the heat exchanger and potentially block it. The low metal ion concentrations can be achieved by employing a nitric acid of low metal ion content, and sluicing out a portion of the circulating acid continuously or periodically and replacing it by fresh sulfuric acid of comparable or higher concentration having a low metal ion content.

Nevertheless, should solid metal sulfates be formed at any point by way of exception, these can be dissolved again with a sulfuric acid having a concentration of greater than 80 wt. %, and preferably greater than 96 wt. % of $H_2SO_4$.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

Comparison Example

A process for the preparation of nitrobenzene by adiabatic nitration was operated with a reaction zone which had a dispersing element at the inlet for thorough mixing of benzene and mixed acid, in which a metal content of 46 mg/l of calcium and 950 mg/l of iron was detected in the circulating acid by means of atomic absorption spectrometry. The nitrating process was operated with this circulating acid. The resulting aqueous phase which contained sulfuric acid in the reaction zone had a content of metal ions which form sparingly soluble metal sulfates, based on the volume of the aqueous phase containing sulfuric acid, of 950 mg/l.

A nitric acid which contained 29 mg/l of calcium and 5 mg/l of iron was then employed for the adiabatic nitration. Due to the consumption of this nitric acid during the nitration of the benzene and the complete recycling of the circulating acid into the reaction zone, the concentration of the metal ions in the circulating acid increased to 180 mg/l of calcium and 1,200 mg/l of iron. Also, considerable amounts of metal sulfates precipitated out on the dispersing element at the inlet of the reaction zone, as a result of which the pressure loss at the dispersing element increased from 13.5 to 14.5 bar and the possible throughput of sulfuric acid was reduced by 18%. As a result, the productivity of nitrobenzene dropped by 16%. As a result, the installation/equipment had to be shut down and the reaction zone cleaned with 96% strength sulfuric acid in an expensive manner, since cleaning with process condensate which substantially comprises water is not successful.

Example 2

Comparison Example

A process for the preparation of nitrobenzene by adiabatic nitration of benzene with mixed acid was operated with a circulating acid which had a metal content of 70 mg/l of calcium, 20 mg/l of aluminium, 80 mg/l of nickel, 120 mg/l of chromium and 660 mg/l of iron, which may also be described as a total of 950 mg/l of metal ions which form sparingly soluble metal sulfates. No further metal ions which form sparingly soluble metal sulfates were detected by means of atomic absorption spectrometry. The nitrating process was operated with this circulating acid. The aqueous phase containing sulfuric acid in the reaction zone had a content of metal ions which form sparingly soluble metal sulfates, based on the volume of the aqueous phase containing sulfuric acid, of 905 mg/l.

The crude nitrobenzene obtained in the phase separation apparatus was utilized for preheating the benzene in a plate heat exchanger, while the circulating sulfuric acid was recycled completely into the reaction zone. A nitric acid of which the content of metal ions which form sparingly soluble metal sulfates in total of less than 10 mg/l was employed for the nitration over a period of 6 weeks. The aqueous phase containing sulfuric acid in the reaction zone had a content of metal ions which form sparingly soluble metal sulfates, based on the volume of the aqueous phase containing sulfuric acid, of 675 mg/l after 6 weeks.

After 6 weeks, the through-openings of the plate heat exchanger are partly blocked by metal sulfates which have precipitated out. As a result of the through-openings being partially blocked, the amount of crude nitrobenzene produced could not completely flow out through these openings and backed up in the phase separation apparatus, as a result of which the phase separation was impaired. This required that the plate heat exchanger be dismantled and cleaned.

Example 3

Example According to the Invention

A process for the preparation of nitrobenzene by adiabatic nitration of benzene with mixed acid was operated with a circulating acid which had a metal content of 90 mg/l of calcium, 10 mg/l of aluminium, 10 mg/l of nickel, 10 mg/l of chromium and 100 mg/l of iron, or a total of 220 mg/l of metal ions which form sparingly soluble metal sulfates. No further metal ions which form sparingly soluble metal sulfates were detected by means of atomic absorption spectrometry. The nitrating process was operated with this circulating acid. The aqueous phase containing sulfuric acid in the reaction zone had a content of metal ions which form sparingly soluble metal sulfates, based on the volume of the aqueous phase containing sulfuric acid, of 200 mg/l.

The crude nitrobenzene obtained in the phase separation apparatus was utilized for preheating the benzene in a plate heat exchanger.

Over a period of 12 weeks, an amount of 0.9 $m^3$ of circulating acid was continuously sluiced out daily and replaced by 0.7 $m^3$ of a sulfuric acid having a content of 96 wt. % of $H_2SO_4$. The average content of metal ions (i.e. Fe, Cr, Ni, Al and Ca) which form sparingly soluble metal sulfates over this period of time was a total of 50 mg/l for the 96 wt. % strength sulfuric acid employed for the renewal and 1 mg/l for the nitric acid. After the period of 12 weeks, no deposits were formed in the heat exchanger and there was no change in the possible throughput through the reaction zone. After 6 weeks, the aqueous phase containing sulfuric acid in the reaction zone had a content of metal ions which form sparingly soluble metal sulfates, based on the volume of the aqueous phase containing sulfuric acid, of 400 mg/l.

Example 4

A process for the preparation of nitrobenzene by adiabatic nitration of benzene with mixed acid was operated in a two-stage experiment with a circulating acid which initially had a metal content of 600 mg/l of metal ions which form sparingly soluble metal sulfates in the first pass of the experiment (according to the invention), and finally had a metal content of metal ions which form sparingly soluble metal sulfates of 1,350 mg/l in the second pass of the experiment (not according to the invention).

The amount of water to be evaporated by the flash evaporator was approx. 10 tonnes per hour. The temperature and pressure in the flash evaporator were identical in the two passes of the experiment and constant for an industrial scale (i.e. the maximum variation was ±0.5° C. and ±1 mbar). Nevertheless, during the first pass of the experiment a sulfuric acid was obtained which had a concentration of $H_2SO_4$ that was 0.25 wt. % higher than the sulfuric acid obtained during the second pass of the experiment.

Example 5

The experiment in two passes according to Example 4 was repeated. This time, the content of metal ions which form sparingly soluble metal sulfates was 400 mg/l during the first pass of the experiment (according to the invention), and 1,900 mg/l during the second pass of the experiment (not according to the invention). The amount of water to be evaporated by the flash evaporator was approx. 8 tonnes per hour. The temperature and pressure in the flash evaporator were identical in the two passes of the experiment and constant for an industrial scale (i.e. the maximum variation was ±0.5° C. and ±1 mbar). During the first pass of the experiment, a sulfuric acid was obtained which had a concentration of $H_2SO_4$ that was 0.10 wt. % higher than the sulfuric acid obtained during the second pass of the experiment.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the continuous preparation of nitrobenzene comprising adiabatically nitrating benzene with a mixture of sulfuric acid and nitric acid in which the sum of the concentrations in the reaction zone of the metal ions which form sparingly soluble metal sulfates is less than 900 mg/l, based on the volume of the aqueous phase containing sulfuric acid;

separating the reaction mixture obtained in the nitration step into an aqueous phase and an organic phase;

evaporating water out of the aqueous phase;

recycling at least a portion of the resultant concentrated sulfuric acid into the nitration step; and additionally introducing sulfuric acid having a concentration of greater than 65% into the nitration step.

2. The process according to claim 1, in which the reaction zone for adiabatically nitrating benzene has at least two dispersing elements.

3. The process according to claim 1, wherein said nitric acid employed in the nitrating step contains less than 10 mg/l of metal ions which form sparingly soluble metal sulfates.

4. The process according to claim 1, wherein said sulfuric acid which is additionally introduced into the nitration step contains less than 100 mg/l of metal ions which form sparingly soluble metal sulfates.

5. The process according to claim 1, wherein said organic phase obtained in the phase separation is used to heat the benzene which is fed to the reaction zone.

6. The process according to claim 1, in which the metal ions which form sparingly soluble metal sulfates are Al, Ca, Cr, Mg, Mn, Fe, Co, Ni, Cu, Sr, Cd and/or Ba and the total content of these metal ions in the reaction zone is less than 800 mg/l, based on the volume of the aqueous phase containing sulfuric acid.

* * * * *